US00PP13808P29

(12) United States Plant Patent
Westhoff

(10) Patent No.: US PP13,808 P2
(45) Date of Patent: May 13, 2003

(54) PETUNIA PLANT NAMED 'WESPEBA'

(75) Inventor: Heinrich Westhoff, Südlohn-Oeding (DE)

(73) Assignee: Josef + Heinrich Westhoff Gartenbau-Spezialkueturen, Sudlohn-Oeding (DE)

( * ) Notice: Subject to any disclaimer, the term of this patent is extended or adjusted under 35 U.S.C. 154(b) by 0 days.

(21) Appl. No.: 10/162,994

(22) Filed: Jun. 5, 2002

(51) Int. Cl.[7] ..... A01H 5/00
(52) U.S. Cl. ..... Plt./356
(58) Field of Search ..... Plt./356

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Petunia plant named 'Wespeba', characterized by its cascading plant habit; freely branching habit; short internodes, dense and bushy growth habit; and single salverform purple and white bi-colored flowers with undulating petal margins.

1 Drawing Sheet

BOTANICAL CLASSIFICATION/CULTIVAR DESIGNATION

*Petunia×hybrida*, cultivar Wespeba.

BACKGROUND OF THE INVENTION

The present Invention relates to a new and distinct cultivar of Petunia plant, botanically known as *Petunia×hybrida*, and hereinafter referred to by the name 'Wespeba'.

The new Petunia is a product of a planned breeding program conducted by the Inventor in Sudlohn-Oeding, Germany. The new Petunia originated from a cross-pollination made by the Inventor of a proprietary Petunia selection identified as 99 P 38, not patented, as the female, or seed, parent with a proprietary Petunia selection identified as 99 P 88, not patented, as the male, or pollen, parent. The new Petunia was selected by the Inventor in 2000 in a controlled environment in Sudlohn-Oeding, Germany.

Asexual reproduction of the new cultivar by terminal cuttings taken in Sudlohn-Oeding, Germany since 2000, has shown that the unique features of this new Petunia are stable and reproduced true to type in successive generations.

SUMMARY OF THE INVENTION

Plants of the cultivar Wespeba have not been observed under all possible environmental conditions. The phenotype may vary somewhat with variations in environment such as temperature and light intensity without, however, any variance in genotype.

The following traits have been repeatedly observed and are determined to be the unique characteristics of 'Wespeba'. These characteristics in combination distinguish 'Wespeba' as a new and distinct Petunia cultivar:

1. Cascading plant habit.
2. Freely branching habit.
3. Short internodes, dense and bushy growth habit.
4. Single salverform purple and white bi-colored flowers with undulating petal margins.

Plants of the new Petunia differ primarily from plants of the parent selections in flower coloration.

Plants of the cultivar Wespeba can be compared to plants of the Petunia cultivar Brevt, disclosed in U.S. Plant Pat. No. 12,679. However in side-by-side comparisons conducted in Sudlohn-Oeding, Germany, plants of the new Petunia and the cultivar Brevt differed in the following characteristics:

1. Plants of the new Petunia had shorter internodes than plants of the cultivar Brevt.
2. Plants of the new Petunia had shorter petioles than plants of the cultivar Brevt.
3. Plants of the new Petunia had smaller sepals than plants of the cultivar Brevt.
4. Plants of the new Petunia had darker purple-colored flowers than plants of the cultivar Brevt.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Petunia.

The photograph at the top of the sheet comprises a side perspective view of a typical plant of 'Wespeba'.

The photograph at the bottom of the sheet comprises a close-up view of a typical flower of 'Wespeba'.

DETAILED BOTANICAL DESCRIPTION

In the following description, color references are made to The Royal Horticultural Society Colour Chart, 1995 Edition, except where general terms of ordinary dictionary significance are used. Plants used for the photographs and the description were grown in 12-cm containers during the spring and summer for about 20 weeks in a glass-covered greenhouse and under conditions which closely approximate commercial production conditions in Sudlohn-Oeding, Germany. During the production of the plants, day temperatures were about 20 to 25° C. and night temperatures were about 16 to 18° C.

Botanical classification: *Petunia×hybrida* cultivar Wespeba.
Parentage:

*Female parent.*—Proprietary *Petunia×hybrida* selection identified as 99 P 38, not patented.

*Male parent.*—Proprietary *Petunia×hybrida* selection identified as 99 P 88, not patented.

Propagation:

*Type cutting.*—Terminal vegetative cuttings.

*Time to initiate roots.*—About 18 days at 20° C.

*Time to develop roots.*—About 20 to 28 days at 20° C.

*Root description.*—Numerous, fine, fibrous and well-branched.

Plant description:

*Form.*—Annual flowering plant; initially upright, then cascading. Viscid, glandular pubescent. Freely continuous basal branching with lateral branches potentially forming at every node.

*Usage.*—Appropriate for hanging baskets, window boxes and patio containers.

*Plant height* (*from soil level to top of plant plane*).—About 25 cm.

*Plant diameter.*—About 40 cm.

*Stem description.*—Main branches, length: About 65 cm. Main branches, diameter: About 4 to 6 mm. Lateral branches, length: About 15 to 42 cm. Lateral branches, diameter: About 3 mm. Internode length: About 2.8 cm. Texture: Densely pubescent. Color: 144B.

*Foliage description.*—Arrangement: Before flowering, alternate; after flowering, opposite; simple. Length: About 5.8 cm. Width: About 3.4 cm. Shape: Ovate. Apex: Acute. Base: Obtuse. Margin: Entire. Aspect: Flat. Texture, upper and lower surfaces: Densely pubescent. Venation pattern: Pinnate. Petiole length: About 4.3 mm. Petiole diameter: About 2.3 mm. Petiole texture, upper and lower surfaces: Pubescent. Color: Young and mature foliage, upper surface: 146A to 146B. Young and mature foliage, lower surface: 146B. Venation, upper surface: 146A. Venation, lower surface: 146C. Petiole, upper and lower surfaces: 146C.

Flower description:

*Flower type and habit.*—Single salverform flowers; flowers face upward and outward; single, axillary. Flowers persistent. Freely flowering.

*Natural flowering season.*—Long day responsive; flowering from April until frost in the autumn in Germany; flowering continuous during this period.

*Fragrance.*—None detected.

*Flower longevity on the plant.*—About one week.

*Flower size.*—Diameter: About 6.3 cm. Depth (height): About 3.15 cm. Tube length: About 2.6 cm. Throat diameter, distal end: About 1.3 cm. Tube diameter, proximal end: About 4.8 mm.

*Flower buds.*—Length: About 2.7 cm. Diameter: About 5 mm. Shape: Oblong. Color: Towards apex, 145C; mid-section and base, 79D.

*Petals.*—Arrangement/appearance: Single whorl of five petals, fused into flared trumpet. Length from throat: About 3 cm. Width: About 3.2 cm. Shape: Roughly spatulate. Apex: Mostly rounded with emargination. Margin: Entire, undulate. Texture: Smooth, satiny. Color: When opening, upper surface: Margin, about 3 mm in width, 145D; center and towards throat, 70B to 70C. When opening, lower surface: Margin, about 3 mm in width, 145D; center and towards throat, 85A. Fully opened, upper surface: Margin, about 3 mm in width, 155D; center and towards throat, 77B; color becoming closer to 79D with subsequent development. Fully opened, lower surface: Margin, about 3 mm in width, 155D; center and towards throat, 86D. Flower throat (inside): 79A. Flower tube (outside): 79A. Venation, upper and lower surfaces: 72A. Venation, throat and tube: 79A.

*Sepals.*—Arrangement/appearance: Single whorl of five sepals, fused at base; star-shaped. Length: About 1.5 cm. Width: About 4 mm. Shape: Linear. Apex: Rounded, obtuse. Margin: Entire. Texture, upper and lower surfaces: Densely pubescent. Color, upper and lower surfaces: 146B.

*Peduncles.*—Length: About 1.4 cm. Width: About 1.8 mm. Strength: Flexible and wiry, holding flowers outwardly. Texture: Pubescent. Color: 146C.

*Reproductive organs.*—Stamens: Quantity: Five per flower. Anther shape: Four-parted, reniform. Anther length: About 3 mm. Anther width: About 2 mm. Anther color: 90B to 90C. Pollen amount: Moderate. Pollen color: 91A. Pistils: Quantity: One per flower. Pistil length: About 2.2 cm. Stigma shape: Round. Stigma color: 146B; towards margin, 83B. Style length: About 1.5 cm. Style color: 145C. Ovary color: 144A to 144B.

*Seed/fruit.*—Seed and fruit production have not been observed.

Disease/pest resistance: Plants of the new Petunia have not been noted to be resistant to pathogens or pests common to Petunia.

Temperature tolerance: Plants of the new Petunia have been observed to be tolerant to temperatures from 2 to 30° C.

It is claimed:

1. A new and distinct cultivar of Petunia plant named 'Wespeba', as illustrated and described.

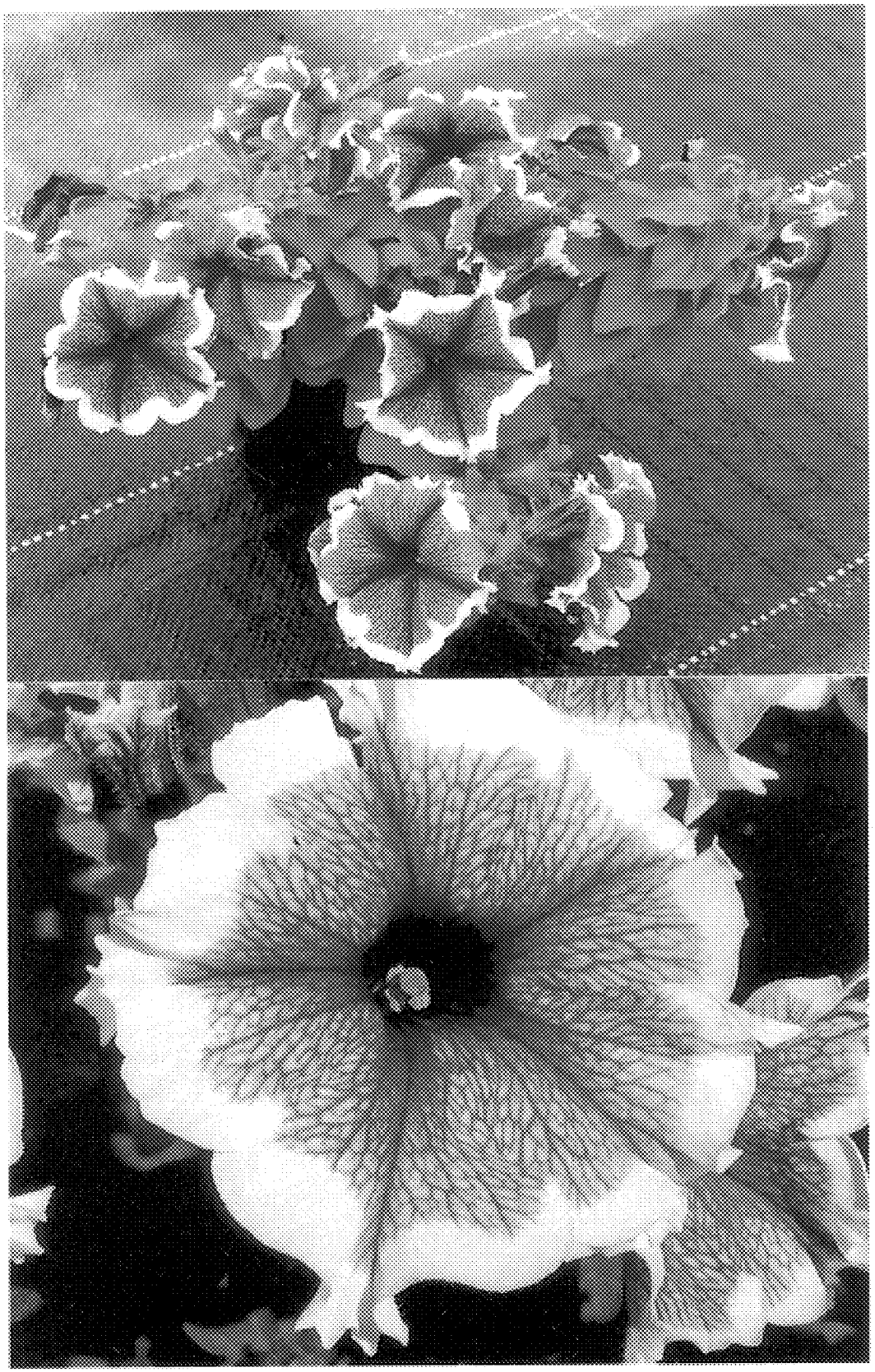

* * * * *